US008202900B2

(12) United States Patent
Lines

(10) Patent No.: US 8,202,900 B2
(45) Date of Patent: *Jun. 19, 2012

(54) METHOD FOR STABILIZING QUERCETIN

(75) Inventor: Thomas Christian Lines, Bereldange (LU)

(73) Assignee: Quercegen Pharmaceuticals LLC, Sudbury, MA (US)

( * ) Notice: Subject to any disclaimer, the term of this patent is extended or adjusted under 35 U.S.C. 154(b) by 641 days.

This patent is subject to a terminal disclaimer.

(21) Appl. No.: 12/212,947

(22) Filed: Sep. 18, 2008

(65) Prior Publication Data

US 2009/0088580 A1    Apr. 2, 2009

Related U.S. Application Data

(60) Provisional application No. 60/976,719, filed on Oct. 1, 2007.

(51) Int. Cl.
*A61K 31/35* (2006.01)

(52) U.S. Cl. .................................... 514/456

(58) Field of Classification Search .................. 514/456
See application file for complete search history.

(56) References Cited

U.S. PATENT DOCUMENTS

| | | | |
|---|---|---|---|
| 5,026,721 A | 6/1991 | Dudrick et al. | |
| 5,804,594 A | 9/1998 | Murad | |
| 5,846,569 A | 12/1998 | Anderson et al. | |
| 6,103,756 A | 8/2000 | Gorsek | |
| 6,203,818 B1 | 3/2001 | Vester | |
| 6,210,701 B1 | 4/2001 | Darland et al. | |
| 6,261,589 B1 | 7/2001 | Pearson et al. | |
| 6,277,426 B1 | 8/2001 | Reust | |
| 6,277,427 B1 | 8/2001 | Husz | |
| 6,299,925 B1 | 10/2001 | Xiong et al. | |
| 6,352,712 B1 | 3/2002 | Lukaczer et al. | |
| 6,491,948 B1 | 12/2002 | Buchholz et al. | |
| 6,511,675 B2 | 1/2003 | Siddiqui et al. | |
| 6,551,629 B1 | 4/2003 | Gorsek | |
| 6,579,544 B1 | 6/2003 | Rosenberg et al. | |
| 6,821,536 B2 | 11/2004 | Lines et al. | |
| 7,041,652 B1 | 5/2006 | Buchholz et al. | |
| 7,270,840 B2 | 9/2007 | Lines et al. | |
| 2002/0025350 A1 | 2/2002 | Siddiqui et al. | |
| 2002/0151599 A1 | 10/2002 | Buchholz et al. | |
| 2003/0054357 A1 | 3/2003 | Young et al. | |
| 2003/0068391 A1 | 4/2003 | Harris et al. | |
| 2004/0126461 A1 | 7/2004 | Lines et al. | |
| 2005/0031737 A1 | 2/2005 | Lines et al. | |
| 2005/0266121 A1 | 12/2005 | Lines et al. | |
| 2007/0148210 A1 | 6/2007 | Lines et al. | |

FOREIGN PATENT DOCUMENTS

| | | |
|---|---|---|
| WO | WO 98/41195 | 9/1998 |
| WO | WO 00/12085 | 3/2000 |
| WO | WO 02/07768 | 1/2002 |
| WO | 2004/037015 | 5/2004 |
| WO | 2008/011363 | 1/2008 |

OTHER PUBLICATIONS

Hye Syn Gwak, et al. "Solubility and physicochemical stability of quercetin in various vehicles" Journal of Korean Pharmaceutical Science, 2004, 34(1), pp. 29-34.

Bors et al., "Flavanoids and Polyphenols: Chemistry and Biology," *Handbook of Antioxidants*, pp. 409-416 (1996).

Chow et al., "Phase I Pharmacokinetic Study of Tea Polyphenols Following Single-dose Administration of Epigallocatechin Gallate and Polyphenon E," Cancer Epidemiology, Biomarkers & Prevention 10:53-58 (2001) XP-002366662.

Crespy et al., "Quercetin, but not Its Glycosides, Is Absorbed from the Rat Stomach," Journal of Agricultural and Food Chemistry, vol. 50, pp. 68-621 (2002).

Dequan et al., "Survey of Bioflavonoids," Food and Fermentation Industries, 25(16): 52-56 (1999) (Translation of English Abstract).

Erlund et al., "Pharmacokinetics of Quercetin from Quercetin Aglycone and Rutin in Healthy Volunteers," Eur. J. Clin. Pharmacol., 56:545-553 (2000).

Guardia et al., "Anti-Inflammatory Properties of Plant Flavinoids. Effect of Rutin, Quercetin and Hesperidin on Adjuvant Arthritis in Rat," Il Farmaco, 56: 683-687 (2001).

Koo et al., "Pharmacological Effects of Green Tea on the Gastrointestinal System," European Journal of Pharmacology 500:177-184 (2004).

Min et al., "The Chemistry and Medical Application of Tea Polyphenol," Hubei Chemical Industry, 2001, 3, 29-31 (Translation of English Abstract).

Saucier et al., "Synergetic Activity of Catechin and Other Antioxidants," Journal of Agricultural and Food Chemistry, 47(11): 4491-4494 (1999).

Sesink et al., "Quercetin Glucuronides but Not Glucosides Are Present in Human Plasma After Consumption of Quercetin-3-Glucoside or Quercetin-4-Glucoside," Human Nutrition and Metabolism Research Communication, pp. 1938-1941 (2001).

Thomas et al., "Ascorbate and Phenolic Antioxidant Interations in Prevention of Liposomal Oxidation," Lipids 27(7) (1992).

Walle et al., "Quercetin Glucosides Are Completely Hydrolyzed in Ileostomy Patients before Absorption," Human Nutrition and Metabolism Research Communication, pp. 2658-2661 (2000).

Gwak et al. "Solubility and Physicochemical Stability of Quercetin in Various Vehicles." Journal of Korean Pharmaceutical Science., col. 34, No. 1, 2004, pp. 29-34.

Supplementary European Search Report issued in Application No. 08835871.8-2101 dated Feb. 23, 2011, 6 pages.

*Primary Examiner* — Bernard Dentz

(74) *Attorney, Agent, or Firm* — Occhiuti Rohlicek & Tsao LLP

(57) ABSTRACT

This invention relates to a method for stabilizing quercetin by placing it in a solution containing vitamin B3 and vitamin C and assessing stability of the quercetin in the mixture.

18 Claims, 1 Drawing Sheet

Accelerated Stability Test

METHOD FOR STABILIZING QUERCETIN

BACKGROUND

It is known that certain natural antioxidants, such as quercetin, inhibit both acute and chronic phases of free-radical induced diseases. Further, some natural antioxidants exhibit synergy in their reactions with biologically relevant oxygen species, e.g., hydroxyl radicals, superoxides, oxysulfurs, sulfur dioxide, and nitrogen dioxide.

However, quercetin is unstable when placed in an aqueous solution. It is therefore desirable to develop a method to increase quercetin stability.

SUMMARY

The present invention is based on the unexpected finding that quercetin is much more stable in a solution also containing vitamins B3 and C than in a solution containing only quercetin.

Accordingly, this invention features a method for stabilizing quercetin by placing it in a solution (e.g., an aqueous solution) containing vitamin B3 and vitamin C to form a mixture and then assessing the stability of the quercetin in the mixture after an extended period of time (e.g., two weeks, two month, or one year). In the mixture, which can be in suspended form, quercetin, vitamin B3, and vitamin C preferably have a weight ratio of 1:0.02-1:0.2-2.5 (e.g., 1:0.08:1). The concentration of quercetin can range from 20 mg/L to 10 g/L (e.g., 500 mg/L to 2 g/L).

The details of one or more embodiments of the invention are set forth in the description below. Other features or advantages of the present invention will be apparent from the following drawing and detailed description of several embodiments, and also from the appending claims.

DETAILED DESCRIPTION

Figure 1:
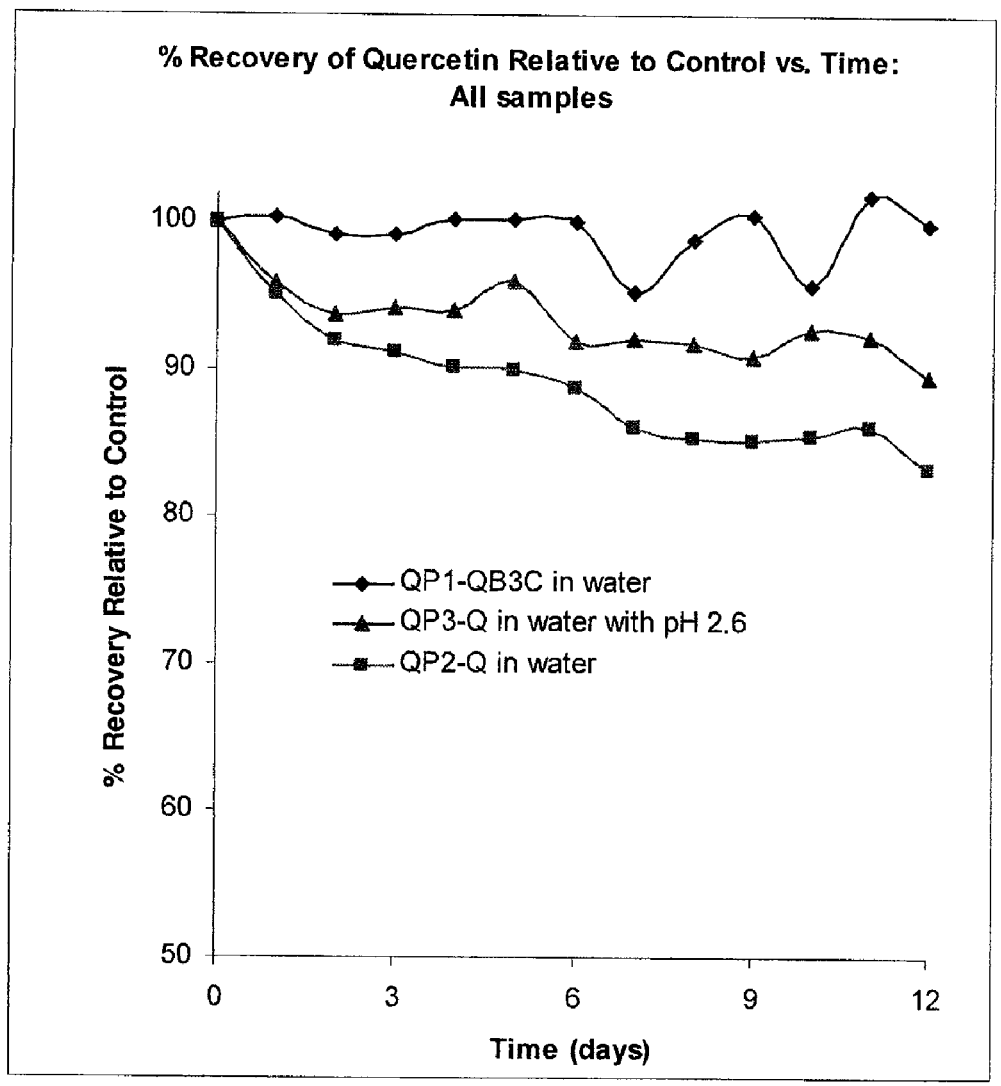
FIG. 1 is a chart showing stability of quercetin in two aqueous solutions containing quercetin alone (QP2-Q), and quercetin, vitamin B3, and vitamin C (QP1-QB3C), respectively, and an acidic solution containing quercetin alone (QP3-Q).

One can stabilize quercetin by either dissolving or suspending it in a solution containing vitamin B3 and vitamin C to form a mixture.

The weight ratio between quercetin, vitamin B3, and vitamin C in the mixture can be 1:0.02-1:0.2-2.5, or any ratio in between. For example, the weight ratio can be 1:0.04-0.5:0.3-2.0, 1:0.05-0.3:0.4-1.5, 1:0.05-0.2:0.5-1, and 1:0.1-0.2:0.5-1. Preferred ratios include 1:0.02:1, 1:0.04:1, 1:0.08:1, 1:0.05:1.5, and 1:0.16:1. The term "quercetin" refers to both quercetin aglycon and quercetin derivatives, e.g., quercetin-3-O-glucoside, quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, which are absorbed in the body. The quantity of quercetin mentioned above refers to that of quercetin aglycon or the quercetin moiety of a quercetin derivative. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil). "Vitamin B3" mentioned herein includes vitamin B3 in its various forms, including niacinamide, nicotinic acid, nicotinamide, inositol hexaniacinate. "Vitamin C" mentioned herein includes vitamin C (i.e., L-ascorbic acid, D-ascorbic acid, or both) and its salts (e.g., sodium ascorbate).

The vitamin B3/vitamin C solution can be prepared by dissolving vitamin B3 and vitamin C in a suitable solvent, such as a pure solvent (e.g., water) or a mixture of two or more solvents. One or more quercetins are then dissolved or suspended in the vitamin B3/vitamin C solution to form a mixture. The mixture can be stored at a suitable temperature (e.g., 20 or 25° C.) for an extended period of time (e.g., two weeks or two month). During the storage, the quercetin content in the mixture is determined periodically (e.g., every 24 hours or every week) via conventional methods, e.g., HPLC, to assess quercetin stability.

Without further elaboration, it is believed that the above description has adequately enabled the present invention. The following example is, therefore, to be construed as merely illustrative, and not limitative of the remainder of the disclosure in any way whatsoever.

Stability of Quercetin and Quercetin/Vitamine B3/Vitamine C in Aqueous Solutions An aqueous solution containing 0.1% (w/v) quercetin (coded "QP2-Q") was prepared, kept in 12 sealed 60-ml glass bottles, i.e., bottles 1-12, and incubated at 75° C. More specifically, 50 ml of the solution were placed in each glass bottle. Quercetin contents in bottles 1-12 were determined by HPLC on day 1 to day 12, respectively. They were compared with the quercetin content on day 0 to obtain "% Recovery Relative to Control," shown in FIG. 1. as follows:

% Recovery Relative to Control=(Quercetin content on day $X$)/(Quercetin content on day 0)

The same analysis as described above was applied to an aqueous solution containing quercetin, vitamin B3, and vitamin C at a ratio of 1:0.08:1 by weight (coded "QP1-QB3C") and to an acidic solution (pH 2.6) containing 0.1% (w/v) quercetin (coded "QP3-Q"). Based on the results thus obtained, stability curves were prepared. Also see FIG. 1.

The quercetin contents in QP1-QB3C remained unchanged during the 12-day incubation period. By contrast, the quercetin contents in QP2-Q and QP3-Q decreased by about 15% and 10% respectively during the 12-day incubation. These results indicate that quercetin was stabilized by the presence of vitamin B3 and vitamin C in the solution.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for stabilizing quercetin, comprising placing quercetin in a solution containing vitamin B3 and vitamin C to form a mixture, wherein the quercetin in the mixture is stable for at least 12 days.

2. The method of claim 1, wherein a weight ratio between quercetin, vitamin B3, and vitamin C is 1:0.02-1:0.2-2.5.

3. The method of claim 2, wherein the weight ratio is 1:0.05-0.2:0.5-1.

4. The method of claim 2, wherein the weight ratio is 1:0.1-0.2:0.5-1.

5. The method of claim 2, wherein the weight ratio is 1:0.04:1.

6. The method of claim 2, wherein the weight ratio is 1:0.08:1.

7. The method of claim 1, wherein the mixture is in suspended form.

8. The method of claim 1, wherein quercetin has a concentration in the mixture from 20 mg/L to 10 g/L.

9. The method of claim 8, wherein the concentration is 500 mg/L to 2 g/L.

10. The method of claim 1, wherein the solution is an aqueous solution.

11. The method of claim 10, wherein a weight ratio between quercetin, vitamin B3, and vitamin C is 1:0.02-1:0.2-2.5.

12. The method of claim 11, wherein the weight ratio is 1:0.05-0.2:0.5-1.

13. The method of claim 11, wherein the weight ratio is 1:0.1-0.2:0.5-1.

14. The method of claim 11, wherein the weight ratio is 1:0.04:1.

15. The method of claim 11, wherein the weight ratio is 1:0.08:1.

16. The method of claim 10, wherein the mixture is in suspended form.

17. The method of claim 10, wherein quercetin has a concentration in the mixture from 20 mg/L to 10 g/L.

18. The method of claim 8, wherein the concentration is 500 mg/L to 2 g/L.

* * * * *